(12) United States Patent
Li et al.

(10) Patent No.: US 12,291,573 B2
(45) Date of Patent: May 6, 2025

(54) APPLICATION OF A NANOBODY TARGETING ON IL-6RA

(71) Applicant: INSTITUTE OF HEALTH AND MEDICINE, HEFEI COMPREHENSIVE NATIONAL SCIENCE CENTER, Anhui (CN)

(72) Inventors: Bofeng Li, Anhui (CN); Tengchuan Jin, Anhui (CN); Jiaojiao Qian, Anhui (CN)

(73) Assignee: INSTITUTE OF HEALTH AND MEDICINE, HEFEI COMPREHENSIVE NATIONAL SCIENCE CENTER, Anhui (CN)

( * ) Notice: Subject to any disclaimer, the term of this patent is extended or adjusted under 35 U.S.C. 154(b) by 0 days.

(21) Appl. No.: 18/642,478

(22) Filed: Apr. 22, 2024

(65) Prior Publication Data
US 2024/0343816 A1    Oct. 17, 2024

Related U.S. Application Data

(63) Continuation of application No. PCT/CN2023/124570, filed on Oct. 13, 2023.

(30) Foreign Application Priority Data

Oct. 31, 2022   (CN) .......................... 202211342568.2

(51) Int. Cl.
| | | |
|---|---|---|
| C07K 16/28 | (2006.01) | |
| A61K 39/00 | (2006.01) | |
| A61P 1/16 | (2006.01) | |

(52) U.S. Cl.
CPC ............ *C07K 16/2866* (2013.01); *A61P 1/16* (2018.01); *A61K 2039/505* (2013.01); *C07K 2317/52* (2013.01); *C07K 2317/565* (2013.01); *C07K 2317/569* (2013.01); *C07K 2317/76* (2013.01)

(58) Field of Classification Search
None
See application file for complete search history.

(56) References Cited

U.S. PATENT DOCUMENTS 10,618,964 B2 *   4/2020   Compernolle ..... C07K 16/2866

FOREIGN PATENT DOCUMENTS

| CN | 101528778 A | 9/2009 |
|---|---|---|
| CN | 105399828 A | 3/2016 |
| CN | 110903393 A | 3/2020 |
| CN | 112778416 A | 5/2021 |
| RU | 2603269 C1 | 11/2016 |
| WO | WO2008071685 A1 | 6/2008 |

OTHER PUBLICATIONS

Finch, et al., "Whole-Molecule Antibody Engineering: Generation of a High-Affinity Anti-IL-6 Antibody with Extended Pharmacokinetics," Journal of Molecular Biology, vol. 411, No. 4, Aug. 2011, pp. 791-807.
International Search Report dated Dec. 21, 2023 in International Application No. PCT/CN2023/124570, 12 pages.

* cited by examiner

*Primary Examiner* — Marianne P Allen
(74) *Attorney, Agent, or Firm* — Lee & Hayes, P.C.

(57) ABSTRACT

The present invention discloses a nanobody targeting IL-6Rα protein and uses thereof, wherein the heavy chain variable region of the nanobody comprises three complementary determining regions, CDR1, CDR2, and CDR3, wherein CDR1 has an amino acid sequence as shown in SEQ ID NO. 2, CDR2 has an amino acid sequence as shown in SEQ ID NO. 3, and CDR3 has an amino acid sequence as shown in SEQ ID NO. 4. With high affinity to IL-6Rα protein and high stability and water solubility, the nanobody can be used in the development of pharmaceutical compositions for the treatment of IL-6-mediated related diseases or conditions, as well as in the development of reagents or kits for the detection of IL-6Rα, which can provide potentially highly effective antibodies for the study of IL-6-mediated related diseases, and provide new therapeutic strategies and targets for autoimmune diseases or tumors.

13 Claims, 9 Drawing Sheets

Specification includes a Sequence Listing.

APPLICATION OF A NANOBODY TARGETING ON IL-6RA

CROSS-REFERENCE TO RELATED APPLICATIONS

This application is a continuation of International Application No. PCT/CN2023/124570, filed on Oct. 13, 2023, which claims the priority and benefit of patent application No. 202211342568.2, filed with the State Intellectual Property Office of China on Oct. 31, 2022. The disclosures of the aforementioned applications are hereby incorporated by reference in their entireties.

STATEMENT REGARDING SEQUENCE LISTING

A Sequence Listing associated with this application is being filed concurrently herewith in XML format and is hereby incorporated by reference into the present specification. The XML file containing the Sequence listing is titled "Sequence_Listing.xml", was created on Oct. 24, 2024, and is 8,086 bytes in size.

FIELD OF THE INVENTION

The present invention belongs to the field of biotechnology, and specifically relates to a nanobody targeting IL-6Rα protein and its usage.

BACKGROUND

Interleukin-6 (IL-6) is a cytokine with a variety of biological activities and a key factor in the complex cytokine network of the body, and it has been shown that IL-6 increases in serum under conditions such as the occurrence of inflammation, necrosis, or due to increased secretion of IL-6 by immune cells stimulated by antigens from tumor cells, and that overexpression of IL-6 is often associated with certain diseases.

It has been confirmed by existing studies that IL-6 can act as a pleiotropic factor, specifically, it can stimulate the liver to induce the production of acute phase response proteins, such as C-reactive protein and fibrinogen, during the acute phase response. For example, during the NKT cell-mediated liver inflammation, IL-6 plays a protective role that prevents liver injury, necrosis, and contributes to liver regeneration, where the mechanism is mainly STAT3 signaling. In addition, macrophages are stimulated by lipopolysaccharide (LPS) to secrete some pro-inflammatory cytokines, such as IL-6 and TNF-α, and these inflammatory factors, in turn, activate the typical nuclear factor-κB (NF-κB) pathway, thus creating a positive feedback loop that amplifies the release of inflammatory factors (IL-1β and TNF-α) and exacerbates inflammation. Not only that, IL-6 is also involved in the differentiation of myeloid-derived suppressor cells (MDSC), and by acting as a second signal required for MDSC differentiation, it can lead to pathological activation of immature myeloid cells, thus promoting MDSC accumulation. All of the above indicate that IL-6 plays an important role in the development of inflammation and cell differentiation, and therefore leads to the development of various diseases once IL-6 is released uncontrollably and continuously.

Currently, monoclonal antibody therapy remains a specific therapeutic option for targeting IL-6, but monoclonal antibodies have some disadvantages such as high molecular weight and difficulty in crossing the tissue barrier, which has led to the development of nanobodies targeting IL-6. Although nanobodies targeting IL-6 are still in the preclinical and clinical development stage, the advantages of nanobodies (e.g., small molecular weight and high tissue penetration) have opened up more possibilities for researchers and strengthened their determination to develop them.

In addition, the existing therapeutic antibodies (specifically targeting IL-6) are expensive, and the proportion of the beneficiary population is very small, so there is a great urgency for the introduction of lower-cost nanobodies, which will bring more hope to patients with IL-6-related diseases.

The present invention is dedicated to the elucidation of a nanobody targeting IL-6Rα protein and its use to provide new targets for the treatment of tumors and autoimmune diseases.

SUMMARY OF THE INVENTION

In view of the above, it is necessary for the present invention to provide a nanobody targeting IL-6Rα protein, which has a high affinity for IL-6Rα protein, and thus is able to provide a wider range of therapeutic strategies for the study of IL-6-related diseases, and open up new therapeutic targets for the treatment of tumors and autoimmune diseases.

In order to realize the above objects, the present invention adopts the following technical solution.

The present invention provides a nanobody targeting an IL-6Rα protein, and the heavy chain variable region of the nanobody comprises three complementary determining regions, CDR1, CDR2, and CDR3, wherein CDR1 has an amino acid sequence as shown in SEQ ID NO.2, CDR2 has an amino acid sequence as shown in SEQ ID NO.3, and CDR3 has an amino acid sequence as shown in SEQ ID NO.4;

preferably, the IL-6Rα protein is a human-derived IL-6Rα protein or a murine-derived IL-6Rα protein.

```
SEQ ID NO. 2:
TIHGVTLDWYAV

SEQ ID NO. 3:
ISSSDGS

SEQ ID NO. 4:
AMVFTTAQAMGVPFHDFEYDYW.
```

In a further embodiment, CDR1 has an amino acid sequence with at least 80% sequence identity to SEQ ID NO.2;
CDR2 has an amino acid sequence with at least 80% sequence identity to SEQ ID NO.3;
CDR3 has an amino acid sequence with at least 80% sequence identity to SEQ ID NO.4.
In a further embodiment, the nanobody has an amino acid sequence as shown in SEQ ID NO.1.

```
SEQ ID NO. 1:
QLQLVESGGGLVRPGGSLRLSCTIHGVTLDWYAVGWFRQAPGKEREGVS
CISSSDGSTYYADSVKGRFTISRDNVKNTMYLQMNSLKPEDTAVYYCAM
VFTTAQAMGVPFHDFEYDYWGPGTQVTVSS.
```

In a further embodiment, the nanobody has an amino acid sequence with at least 80% sequence identity to SEQ ID NO.1.

In a further embodiment, the nanobody further comprises an Fc domain of IgG;
preferably, the Fc domain is an IgG1 Fc domain;
preferably, the IgG1 Fc domain is a human IgG1 Fc domain;
preferably, the amino acid sequence of the human IgG1 Fc domain is as shown in SEQ ID NO.5.

SEQ ID NO. 5:
PKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTV

DKSRWQQGNVFSCSVMHEALHNHYTQKSLSLSPGK.

In a further embodiment, the amino acid sequence of the nanobody is shown in SEQ ID NO.6.

SEQ ID NO. 6:
QLQLVESGGGLVRPGGSLRLSCTIHGVTLDWYAVGWFRQAPGKEREGVS

CISSSDGSTYYADSVKGRFTISRDNVKNTMYLQMNSLKPEDTAVYYCAM

VFTTAQAMGVPFHDFEYDYWGPGTQVTVSSPKSCDKTHTCPPCPAPELL

GGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEA

LHNHYTQKSLSLSPGK.

The present invention further provides a bi-epitope antibody comprising a first half antibody and a second half antibody, the first half antibody being a nanobody as described hereinbefore, and the second half antibody having a different epitope from the first half antibody;
preferably, the first half antibody and the second half antibody are connected to each other by a peptide linker;
preferably, the connecting fragment of the peptide linker is (GGGGS as shown in SEQ ID NO.7) n, wherein n is a positive integer.

The present invention further provides a nucleotide molecule encoding the nanobody of the foregoing or the bi-epitope antibody of the foregoing.

The present invention further provides an expression vector, which contains the nucleotide molecule of the foregoing.

The present invention further provides a host cell, and the host cell is a host cell for expression of an exogenous protein, which contains the expression vector of the foregoing;
preferably, the host cell is a bacterial, yeast, insect cell or mammalian cell.

The present invention further provides the use of the nanobody as hereinbefore described or the bi-epitope antibody of the foregoing in the preparation of a pharmaceutical composition for the treatment of an IL-6 mediated disease or condition; or the use in the preparation of an IL-6Rα protein detection reagent or kit.

In a further embodiment, the IL-6 mediated disease or condition comprises at least one of hepatitis, crohn's disease, Rheumatoid arthritis (RA), meningitis.

The present invention further provides a pharmaceutical composition, which comprises the nanobody as hereinbefore described or the bi-epitope antibody of the foregoing, further comprising at least one pharmaceutically acceptable excipient.

The present invention further provides an IL-6Rα protein detection reagent or kit, which comprises the nanobody of the foregoing or the bi-epitope antibody of the foregoing.

The present invention further provides the use of the nanobody as hereinbefore described, the bi-epitope antibody as hereinbefore described, the nucleotide molecule as hereinbefore described, the expression vector as hereinbefore described, the host cell as hereinbefore described, and the pharmaceutical composition as hereinbefore described in preventing and/or treating an IL-6 mediated disease or condition.

In a further embodiment, the IL-6 mediated disease or condition comprises at least one of hepatitis, crohn's disease, Rheumatoid arthritis (RA), meningitis.

The present invention further provides a method of preventing and/or treating an IL-6 mediated disease or condition, which comprises:
administering to a subject suffering from or suspected of suffering from an IL-6-mediated disease or condition an effective amount of at least one of below:
the nanobody as hereinbefore described, the bi-epitope antibody as hereinbefore described, the nucleotide molecule as hereinbefore described, and the pharmaceutical composition as hereinbefore described.

In a further embodiment, the IL-6 mediated disease or condition comprises at least one of hepatitis, crohn's disease, Rheumatoid arthritis (RA), meningitis.

The present invention further provides the use of the nanobody as hereinbefore described, the bi-epitope antibody as hereinbefore described, the nucleotide molecule as hereinbefore described, the expression vector as hereinbefore described, the host cell as hereinbefore described, and the pharmaceutical composition as hereinbefore described in inhibiting the secretion of inflammatory factors by macrophages in an organism or in vitro.

In a further embodiment, the inflammatory factors comprise IL-1β.

The present invention further provides a method of inhibiting the secretion of inflammatory factors by macrophages in an organism or in vitro, which comprises:
administering to an organism having a need to inhibit the secretion of inflammatory factors the nanobody as hereinbefore described and/or the bi-epitope antibody as hereinbefore described and/or the pharmaceutical composition as hereinbefore described so as to inhibit the secretion of inflammatory factors by macrophages contained in the organism; or
contacting the nanobody as hereinbefore described and/or the bi-epitope antibody as hereinbefore described and/or the pharmaceutical composition as hereinbefore described with the macrophages so as to inhibit the secretion of inflammatory factors in vitro.

In a further embodiment, the inflammatory factors comprise IL-1β.

The present invention further provides the use of the nanobody as hereinbefore described, the bi-epitope antibody as hereinbefore described, the nucleotide molecule as hereinbefore described, the expression vector as hereinbefore described, the host cell as hereinbefore described, and the pharmaceutical composition as hereinbefore described in inhibiting the developmental differentiation of myeloid precursor cells into MDSC cells in vivo or in vitro.

The present invention further provides a method of inhibiting the developmental differentiation of myeloid precursor cells into MDSC cells in vivo or in vitro, which comprises:

administering to an organism having a need to inhibit the developmental differentiation of myeloid precursor cells into MDSC cells the nanobody as hereinbefore described and/or the bi-epitope antibody as hereinbefore described and/or the pharmaceutical composition as hereinbefore described so as to inhibit the developmental differentiation of myeloid precursor cells into MDSC cells contained in the organism; or contacting the nanobody as hereinbefore described and/or the bi-epitope antibody as hereinbefore described and/or the pharmaceutical composition as hereinbefore described with the myeloid precursor cells so as to inhibit the developmental differentiation of myeloid precursor cells into MDSC cells in vitro.

The beneficial effects of the present invention are shown as follows:

The nanobody in the present invention is capable of binding IL-6Rα protein with high affinity with an affinity KD value of up to $6.33 \times 10^{-9}$ M; and the nanobody is capable of binding not only human-derived IL-6Rα, but also murine-derived IL-6Rα protein, with cross-species activity.

The binding of the nanobody to IL-6Rα protein provides a broader therapeutic strategy for the study of IL-6-mediated diseases or conditions, and also opens up new therapeutic targets for the treatment of tumors and autoimmune diseases.

Additional aspects and advantages of the present invention will be given, in part, as will become apparent from the following description, or as will be learned through the practice of the invention.

BRIEF DESCRIPTION OF THE DRAWINGS

The foregoing and/or additional aspects and advantages of the present invention will become apparent and readily understood from the description of the embodiments in conjunction with the following accompanying drawings, wherein.

DETAILED DESCRIPTION OF THE INVENTION

It is to be understood that the embodiments of the present invention are not to be limited to the following described exemplary embodiments, and the embodiments described below are exemplary and are intended to be used only for the purpose of explaining the present invention and are not to be construed as a limitation of the invention.

Unless otherwise defined, all technical and scientific terms used herein have the same meaning as commonly understood by those skilled in the art belonging to the present invention. The terms used herein in the specification of the present invention are used only for the purpose of describing specific embodiments and are not intended to limit the present invention.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Further, unless otherwise required by context, singular terms shall include pluralities and plural terms shall include the singular.

As employed above and throughout the disclosure, the following terms and abbreviations, unless otherwise indicated, shall be understood to have the following meanings.

Definitions

In the present disclosure the singular forms "a," "an," and "the" include the plural reference, and reference to a particular numerical value includes at least that particular value, unless the context clearly indicates otherwise. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

In the specification and claims, the term "bi-epitope antibody" refers to a bispecific monoclonal antibody (BsMAb, BsAb), which is an artificial protein that can simultaneously bind to two different types of antigen or two different epitopes on the same antigen. As used herein the term "Half antibody" is one half of an antibody which comprises a heavy chain and a light chain, which is a common byproduct in bispecific antibody (bsAb) production and in many cases it represents the major product-related impurity.

In the specification and claims, the numbering of the amino acid residues of CDR1-3 of the nanobody is that of the Eu index as in Kabat et al., Sequences of Proteins of Immunological Interest, 5th Ed. Public Health Service, National Institutes of Health, Bethesda, Md. (1991).

The term "expression vector" as used herein refers to a recombinant DNA molecule containing a desired coding sequence and appropriate nucleic acid sequences necessary for the expression of the operably linked coding sequence in a particular host organism.

A nucleic acid molecule is "operably linked" or "operably attached" when it is placed into a functional relationship with another nucleic acid molecule. For example, a promoter or enhancer is operably linked to a coding sequence of nucleic acid if it affects the transcription of the sequence; or a ribosome binding site is operably linked to a coding sequence of nucleic acid if it is positioned so as to facilitate translation.

As used herein, the term "host cell" refers to any eukaryotic or prokaryotic cell (e.g., bacterial cells such as *E. coli*, CHO cells, yeast cells, mammalian cells, avian cells, amphibian cells, plant cells, fish cells, and insect cells), whether located in vitro or in situ, or in vivo.

As used herein, the term "Fc region" refers to a C-terminal region of an immunoglobulin heavy chain. The "Fc region" may be a native sequence Fc region or a variant Fc region. In some embodiments, variants comprise only portions of the Fc region and can include or not include the carboxy-terminus. The Fc region of an immunoglobulin generally comprises two constant domains, CH2 and CH3. In some embodiments, variants having one or more of the constant domains are contemplated. In other embodiments, variants without such constant domains (or with only portions of such constant domains) are contemplated.

As used herein, "at least 80% sequence identity" means an amino acid sequence comprising one to more amino acid additions, deletions, or substitutions to have greater than or equal to 80%, but less than 100% amino acid sequence identity to a reference sequence, and exhibiting similar IL-6Rα protein specific binding.

As used herein, an "amino acid substitution" refers to the replacement of at least one existing amino acid residue in a given amino acid sequence with another different "replacement" amino acid residue. The replacement residue or residues may be "naturally occurring amino acid residues" (i.e., encoded by the genetic code) and selected from: alanine (Ala); arginine (Arg); asparagine (Asn); aspartic acid (Asp); cysteine (Cys); glutamine (Gin); glutamic acid (Glu); glycine (Gly); histidine (H is); isoleucine (lie): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991).

The term "binding affinity" refers to the equilibrium dissociation constant (expressed in units of concentration) associated with IL-6Rα protein-nanobody binding interaction. The binding affinity is directly related to the ratio of the kinetic off-rate (generally reported in units of inverse time, e.g., seconds$^{-1}$) divided by the kinetic on-rate (generally reported in units of concentration per unit time, e.g., molar/second).

As used herein, the term "antibody" is used interchangeably with "immunoglobulin" or "Ig," is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity or functional activity. Single chain antibodies, chimeric antibodies, and nanobodies, as well as chimeric or CDR-grafted single chain antibodies, and the like, comprising portions derived from different species, are also encompassed by the present invention and the term "antibody". The various portions of these antibodies can be joined together chemically by conventional techniques, synthetically, or can be prepared as a contiguous protein using genetic engineering techniques. It is understood that all forms of the antibodies comprising an Fc region (or portion thereof) are encompassed herein within the term "antibody" Furthermore, the antibody may be labeled with a detectable label, immobilized on a solid phase and/or conjugated with a heterologous compound (e.g., an enzyme or toxin) according to methods known in the art.

As used herein, the term "condition" and "disease" are used interchangeably to refer to any condition that would benefit from treatment with the nanobodies of the present invention, including chronic and acute condition or diseases.

A first aspect of the present invention discloses a nanobody targeting IL-6Rα protein, specifically, the present invention provides variable region sequences (VHH) of alpaca-derived heavy chain antibodies capable of binding IL-6Rα protein with high affinity, which are referred to as nanobodies, and which provide potentially highly effective antibodies for the study of IL-6-mediated related diseases, and which can be developed into diagnostic reagents or diagnostic kits and the like, to provide new targets for autoimmune disease treatment.

The heavy chain variable region of the nanobody described herein comprises three complementary determining regions, CDR1, CDR2, and CDR3, wherein CDR1 has an amino acid sequence as shown in SEQ ID NO.2, CDR2 has an amino acid sequence as shown in SEQ ID NO.3, and CDR3 has an amino acid sequence as shown in SEQ ID NO.4. The nanobodies described herein are capable of targeting not only human-derived IL-6Rα proteins, but also murine-derived IL-6Rα proteins, and thus have cross-species activity.

In an exemplary embodiment of the present invention, CDR1 has an amino acid sequence with at least 80% sequence identity to SEQ ID NO.2;

CDR2 has an amino acid sequence with at least 80% sequence identity to SEQ ID NO.3; CDR3 has an amino acid sequence with at least 80% sequence identity to SEQ ID NO.4.

In an exemplary embodiment of the present invention, the nanobody with the highest affinity therein is designated 2S3-3D, which has an amino acid sequence as shown in SEQ ID NO.1.

In a further embodiment, the nanobody further comprises an Fc domain of IgG, specifically, the C-terminus of the nanobody is attached to the Fc domain of lgG to form a recombinant antibody or fusion protein; preferably, the Fc domain is the IgG1 Fc domain; more preferably, the IgG1 Fc domain is the human IgG1 Fc domain; in an exemplary embodiment of the invention, the human IgG1 Fc domain has the amino acid sequence shown in SEQ ID NO.5.

In a further embodiment, the amino acid sequence of the nanobody is shown in SEQ ID NO.6.

In other embodiments, there are some conserved amino acid substitutions in Fc domain or CDRs of the nanobody provided by the present invention.

A second aspect of the present invention discloses a bi-epitope antibody comprising a first half antibody and a second half antibody, the first half antibody being a nanobody as described in the first aspect of the present invention, and the second half antibody being not particularly limited and can be selected according to actual needs, it being noted that the second half antibody has a different epitope from the first half antibody. Therein, the first half antibody and the second half antibody are connected to each other by a linker forming a bi-epitope antibody. It is to be understood that such a linker can be a conventional peptide linker (i.e., a flexible polypeptide chain) in the art with a connecting fragment of (GGGGS as shown in SEQ ID NO.7) n, wherein n is a positive integer, which may be selected according to the actual need, and preferably, n is 2, 3, 4, 5 and the like.

A third aspect of the present invention provides a nucleotide molecule encoding a nanobody as described in the first aspect of the present invention or a bi-epitope antibody as described in the second aspect of the present invention. It is to be understood that the nucleotide molecule may be prepared by conventional preparation methods in the art, such as PCR methods or artificial sequence synthesis and the like, which will not be specifically described herein.

A fourth aspect of the present invention provides an expression vector, which contains the nucleotide molecule as described in the third aspect of the present invention. The expression vector is an expression vector containing appropriate regulatory sequences (e.g. promoter sequences, terminator sequences, marker genes and/or sequences, etc.), which may be of a type of vector conventional in the art, such as a virus or a plasmid, which will not be specifically described herein, and preferably, the expression vector is a plasmid.

A fifth aspect of the present invention provides a host cell, the host cell containing an expression vector as described in the fourth aspect of the present invention. The host cell described herein is a host cell for expression of an exogenous protein as long as it is capable of enabling the above expression vector to be stably replicated and the nucleotide carried can be efficiently expressed. Preferably, the host cell is a bacterial, yeast, insect cell or mammalian cell.

A sixth aspect of the present invention provides the use of the nanobody as described in the first aspect of the present invention or the bi-epitope antibody as described in the second aspect in the preparation of a pharmaceutical composition for the treatment of an IL-6-mediated disease or condition; or the use in the preparation of an IL-6Rα protein detection reagent or kit. By way of example, the pharmaceutical compositions may be inhibitors of the inflammatory factor IL-1β, inhibitors of murine-derived MDSC differentiation, or T-cell-mediated hepatitis therapeutics.

In a further embodiment, the IL-6 mediated disease or condition comprises at least one of hepatitis, crohn's disease, Rheumatoid arthritis (RA), meningitis.

A seventh aspect of the present invention provides a pharmaceutical composition, which comprises the nanobody as described in the first aspect of the present invention or the bi-epitope antibody as described in the second aspect of the present invention, further comprising at least one pharmaceutically acceptable excipient. It will be appreciated that the nanobody or bi-epitope antibody in the pharmaceutical composition is based on a therapeutically effective amount, specifically, an effective amount herein refers to an amount comprising an amount sufficient to prevent or treat a symptom or disease of a medical condition. After use in a particular patient or medical subject, the following changes can occur: an improvement in the condition treated, in the overall health of the patient/subject. The effective amount may also be to a dosage regimen below the maximum dose to avoid significant side or toxic effects. The pharmaceutically acceptable excipients include carriers, excipients, diluents, etc., and the specific types of which may be adapted according to the type of formulation of the pharmaceutical composition, and therefore will not be specifically described herein.

An eighth aspect of the present invention provides an IL-6Rα protein detection reagent or kit, which comprises the nanobody as described in the first aspect of the present invention or the bi-epitope antibody as described in the second aspect. The design of the specific detection reagent or kit can be adjusted according to specific needs, but it is understood that the detection reagent or kit includes at least the nanobody or the bi-epitope antibody of the present invention, so that it is able to specifically bind to the IL-6Rα protein and analyze the IL-6Rα protein in the sample to be tested, in order to obtain the relevant information of IL-6-mediated diseases or conditions, and provide a broader range of therapeutic strategies for the research of IL-6-associated diseases, as well as to open up new therapeutic targets for the treatment of tumors and autoimmune diseases.

A ninth aspect of the present invention provides the use of the nanobody as hereinbefore described, the bi-epitope antibody as hereinbefore described, the nucleotide molecule as hereinbefore described, the expression vector as hereinbefore described, the host cell as hereinbefore described, and the pharmaceutical composition as hereinbefore described in preventing and/or treating an IL-6 mediated disease or condition.

It is to be noted that the IL-6 mediated disease or condition is a disease or condition associated with abnormal levels of the cytokine IL-6, which in the context of the present invention includes, but is not limited to, hepatitis, crohn's disease, Rheumatoid arthritis (RA), meningitis, and the like.

A tenth aspect of the present invention provides a method of preventing and/or treating an IL-6 mediated disease or condition, which comprises:
administering to a subject suffering from or suspected of suffering from an IL-6-mediated disease or condition an effective amount of at least one of below:
the nanobody as hereinbefore described, the bi-epitope antibody as hereinbefore described, the nucleotide molecule as hereinbefore described, and the pharmaceutical composition as hereinbefore described.

A eleventh aspect of the present invention provides the use of the nanobody as hereinbefore described, the bi-epitope antibody as hereinbefore described, the nucleotide molecule as hereinbefore described, the expression vector as hereinbefore described, the host cell as hereinbefore described, and the pharmaceutical composition as hereinbefore described in inhibiting the secretion of inflammatory factors by macrophages in an organism or in vitro.

It is to be noted that the inflammatory factors referred to in the present invention in the context of inhibiting the secretion of inflammatory factors by macrophages include, but are not limited to, IL-1β.

A twelfth aspect of the present invention provides a method of inhibiting the secretion of inflammatory factors by macrophages in an organism or in vitro, which comprises:
administering to an organism having a need to inhibit the secretion of inflammatory factors the nanobody as hereinbefore described and/or the bi-epitope antibody as hereinbefore described and/or the pharmaceutical composition as hereinbefore described so as to inhibit the secretion of inflammatory factors by macrophages contained in the organism; or
contacting the nanobody as hereinbefore described and/or the bi-epitope antibody as hereinbefore described and/or the pharmaceutical composition as hereinbefore described with the macrophages so as to inhibit the secretion of inflammatory factors in vitro.

A thirteenth aspect of the present invention provides the use of the nanobody as hereinbefore described, the bi-epitope antibody as hereinbefore described, the nucleotide molecule as hereinbefore described, the expression vector as hereinbefore described, the host cell as hereinbefore described, and the pharmaceutical composition as hereinbefore described in inhibiting the developmental differentiation of myeloid precursor cells into MDSC cells in vivo or in vitro.

A fourteenth aspect of the present invention provides a method of inhibiting the developmental differentiation of myeloid precursor cells into MDSC cells in vivo or in vitro, which comprises:

administering to an organism having a need to inhibit the developmental differentiation of myeloid precursor cells into MDSC cells the nanobody as hereinbefore described and/or the bi-epitope antibody as hereinbefore described and/or the pharmaceutical composition as hereinbefore described so as to inhibit the developmental differentiation of myeloid precursor cells into MDSC cells contained in the organism; or contacting the nanobody as hereinbefore described and/or the bi-epitope antibody as hereinbefore described and/or the pharmaceutical composition as hereinbefore described with the myeloid precursor cells so as to inhibit the developmental differentiation of myeloid precursor cells into MDSC cells in vitro.

The present invention is hereinafter described by way of specific examples, and it should be noted that the following specific examples are for illustrative purposes only and do not limit the scope of the present invention in any way, and furthermore, if not otherwise indicated, methods without specifically documented conditions or steps are conventional, and the reagents and materials employed are commercially available. Herein, alpacas were immunized with human-derived IL-6Rα protein recombinantly expressed in vitro, and then peripheral blood lymphocytes were isolated and total RNA was extracted from the cells, which was subsequently reverse transcribed into cDNA; then, using the cDNA as a template, the nanobody sequences were amplified with specific primers and a phage display library was constructed; then, the library was screened by using human-derived IL-6Rα, so as to obtain a plurality of nanobodies possessing the ability to specifically bind to IL-6Rα, and the ones with a higher affinity were screened out from the library.

Example 1 Preparation of Immunogen h-IL-6Rα (Human-Derived IL-6Rα)

In this Example, the preparation of immunogen h-IL-6Rα is based on prior art, and the detailed preparation steps are referred to the Chinese patent application No. 202111337977.9 to obtain soluble human IL-6Rα protein.

Example 2 Immunization of Alpaca

Take the soluble human-derived IL-6Rα protein with high purity prepared in Example 1 as the antigen, take 0.2 mg of this antigen and 500 μL of complete Freund's adjuvant as emulsified mixture and give the first intravenous injection to one alpaca of 2-4 weeks of age; and then use this protein with 500 μL of incomplete Freund's adjuvant to strengthen the immunization for three times at three weeks' intervals.

Example 3 Phage Display Library Construction and Screening 20 mL peripheral blood of alpaca was collected by venous blood sampling, and PBMC was isolated by using lymphocyte isolation solution Ficoll 1.077, and RNA was extracted by Trizol operation manual, and reverse transcribed into cDNA by using Oligo (dT), and the VHH gene of alpaca was cloned into pR2 phage by primer amplification and molecular cloning, and the VHH phage library was obtained by transforming TG1.

Phage display screening was performed with the help of helper phages, and the encapsulated immunogen h-IL-6Rα was subjected to two rounds of biopanning. The enriched phages were eluted, transformed, coated with plates, and single clones were picked for ELISA assay of phage binding to protein h-IL-6Rα, and the clones with binding read value >1 were sent for sequencing, cloned into expression vector pTT5, and transfected into 293F cells to express the nanobodies. The amino acid sequences of the nanobodies obtained after two rounds of biopanning are shown in SEQ ID NO.1-4.

Example 4 Preparation of Anti-h-IL-6Rα Nanobodies

The VHH gene of the nanobody was cloned into the expression vector pTT5 by molecular cloning technique, and 293F cells were transfected to express the nanobody. The specific preparation method refers to the Chinese patent application No. 202111337977.9.

Example 5 ELISA for Identification of Antigen-Antibody Binding

The antigen h-IL-6Rα was coated in an immunoplate, and blocking, primary antibody incubation and secondary antibody incubation were employed, etc. After TMB color reaction and termination of color development by concentrated sulfuric acid, the OD450 value was measured by Microplate Reader to determine whether the antigen binds to the antibody.

The detection of antibody binding to the murine-derived antigen m-IL-6Rα was performed in the same way as described above.

Figure 1:
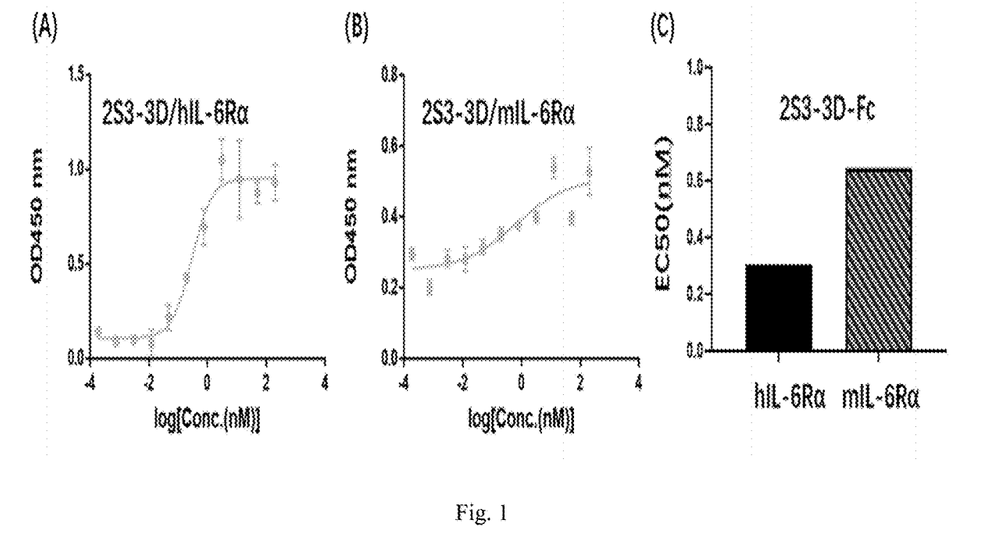
FIG. 1 shows a graph of the results of the identifying the binding of nanobody-Fc to antigen by ELISA in Example 5.

The test results are shown in FIG. 1, in which FIG. 1-(A) shows the ELISA, EC50 results of the Fc-carrying nanobody bound to the human-derived antigen h-IL-6Rα, and FIG. 1-(B) shows the ELISA, EC50 results of the Fc-carrying nanobody bound to the murine-derived antigen m-IL-6Rα, and FIG. 1-(C) shows the bar diagram of the above results. It can be seen that both human-derived antigens or murine-derived antigens can bind well to the nanobodies, among which 2S3-3D-Fc has the best binding ability, indicating that the nanobodies obtained herein have cross-species activity.

Example 6 SPR Characterization of Antigen-Antibody Binding

The binding kinetics experiments for detecting antigen-antibody were carried out by Biocare Molecular Biological Interaction Platform. The antigen h-IL-6Rα was immobilized on CM5 chip (Cytiva, USA), and the blank channel was set as a negative control, and then nanobodies (2S3-3D) with different concentration gradients (250 nM, 125 nM, 62.5 nM, 31.2 nM, and 15.6 nM) were conjugated to it. The binding time was set at 180 s/dissociation time at 200 s. The binding and dissociation of antigen and antibody were observed, and the data were analyzed by the corresponding analysis software.

Figure 2:
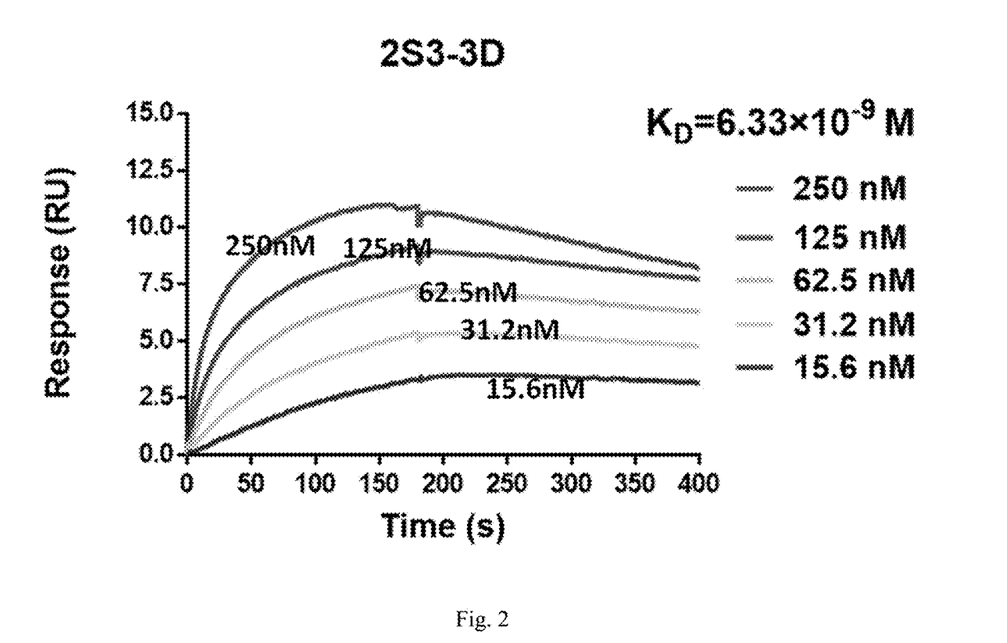
FIG. 2 shows a graph of the results of identifying the binding kinetics of different concentration gradients of the nanobody (2S3-3D) to the antigen h-IL-6Rα by SPR in Example 6.

As shown in FIG. 2, it was found that the nanobodies 2S3-3D could bind to the antigen with nanomolar affinity.

This shows that the nanobodies have high affinity for the antigen and can be used for the detection of IL-6Rα.

Example 7 Nanobody Blocking Secretion of Inflammatory Factors

THP-1 cells (human leukemia monocyte cell line, TIB-202, ATCC, USA) were induced to become macrophages with PMA (Phorbol Ester), and immediately after that, these macrophages were stimulated by the simultaneous addition of 1 μg/mL LPS and 100 μg/mL of antibody (2S3-3D), and then the levels of IL-1β in the supernatants of the cells were measured by using the instructions of the ELISA kit to evaluate the effects of the antibody.

Figure 3:
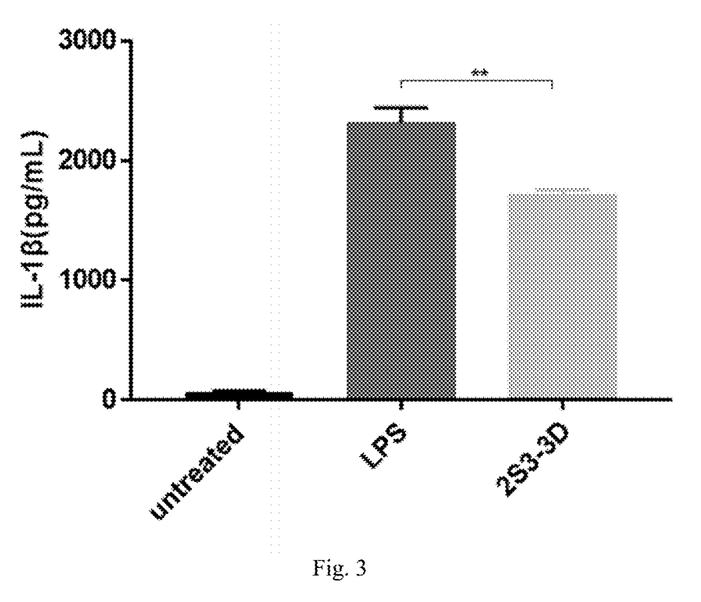
FIG. 3 shows a graph of the results of IL-1β levels in the supernatants of the cells thereof after treatment with the nanobody (2S3-3D) by means of ELISA in Example 7.
Figure 4A:
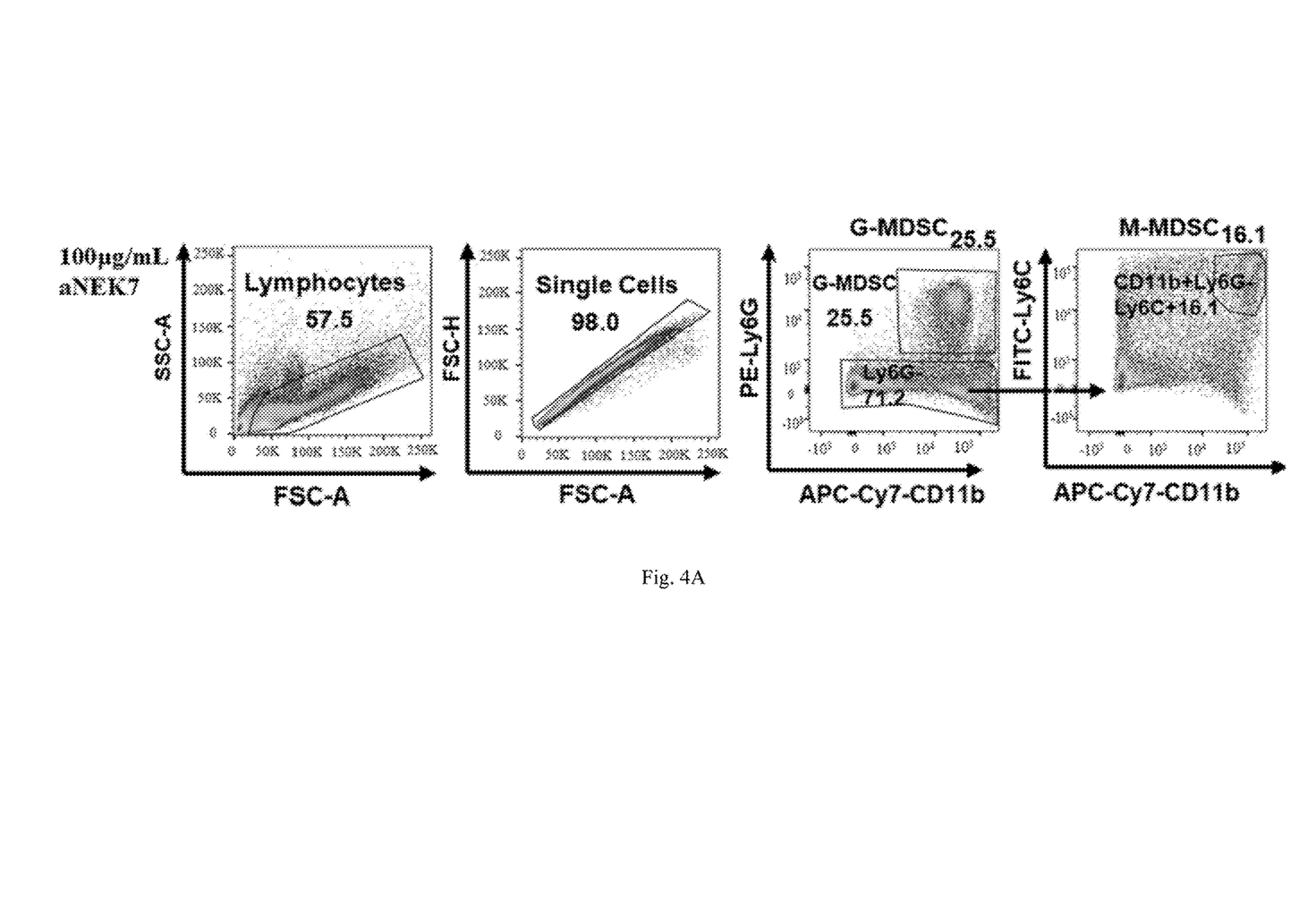
FIG. 4A to FIG. 4E show the results of the staining of MDSC cells after treatment with the nanobody (2S3-3D) detected by means of FACS in Example 8.
Figure 4B:
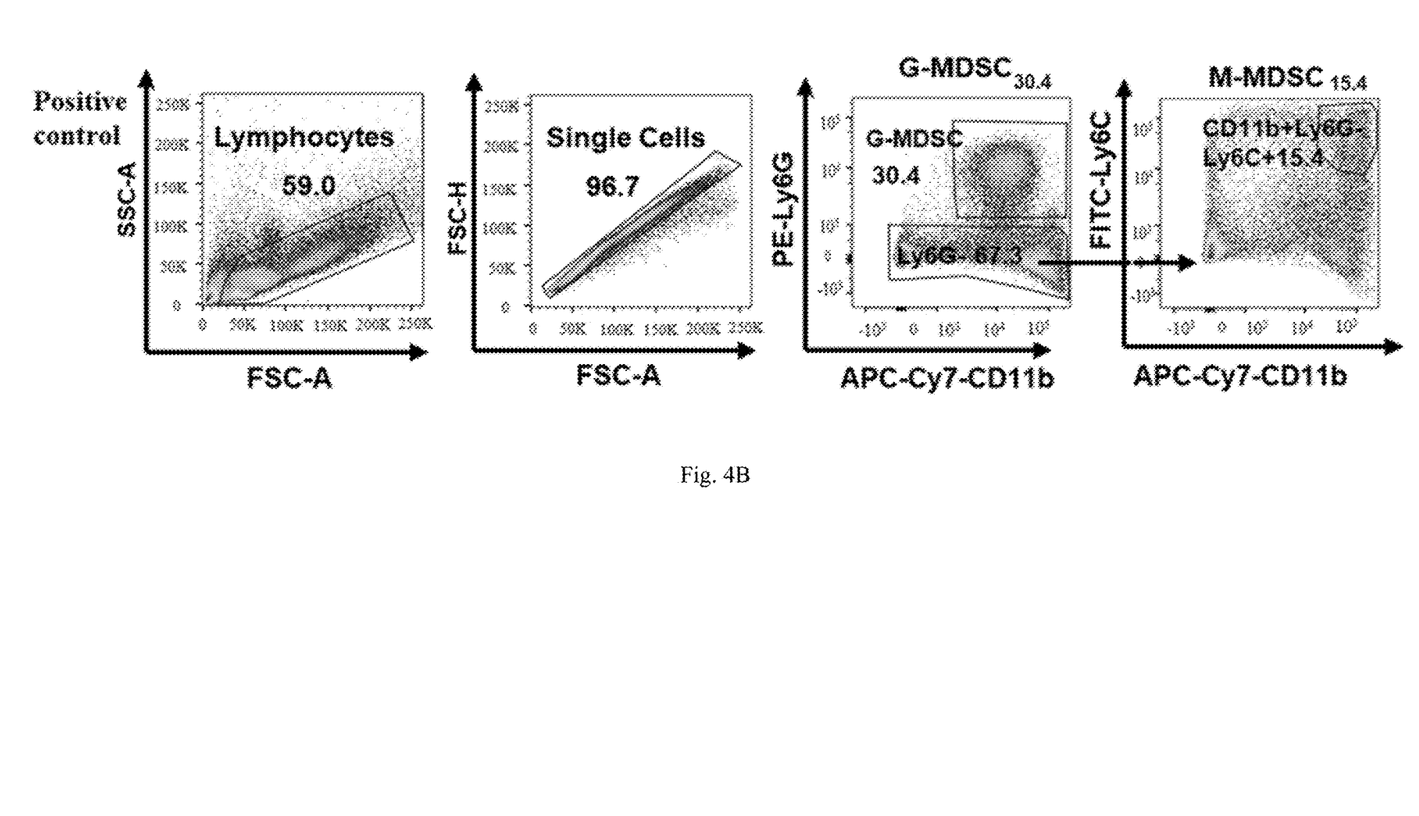
Figure 4C:
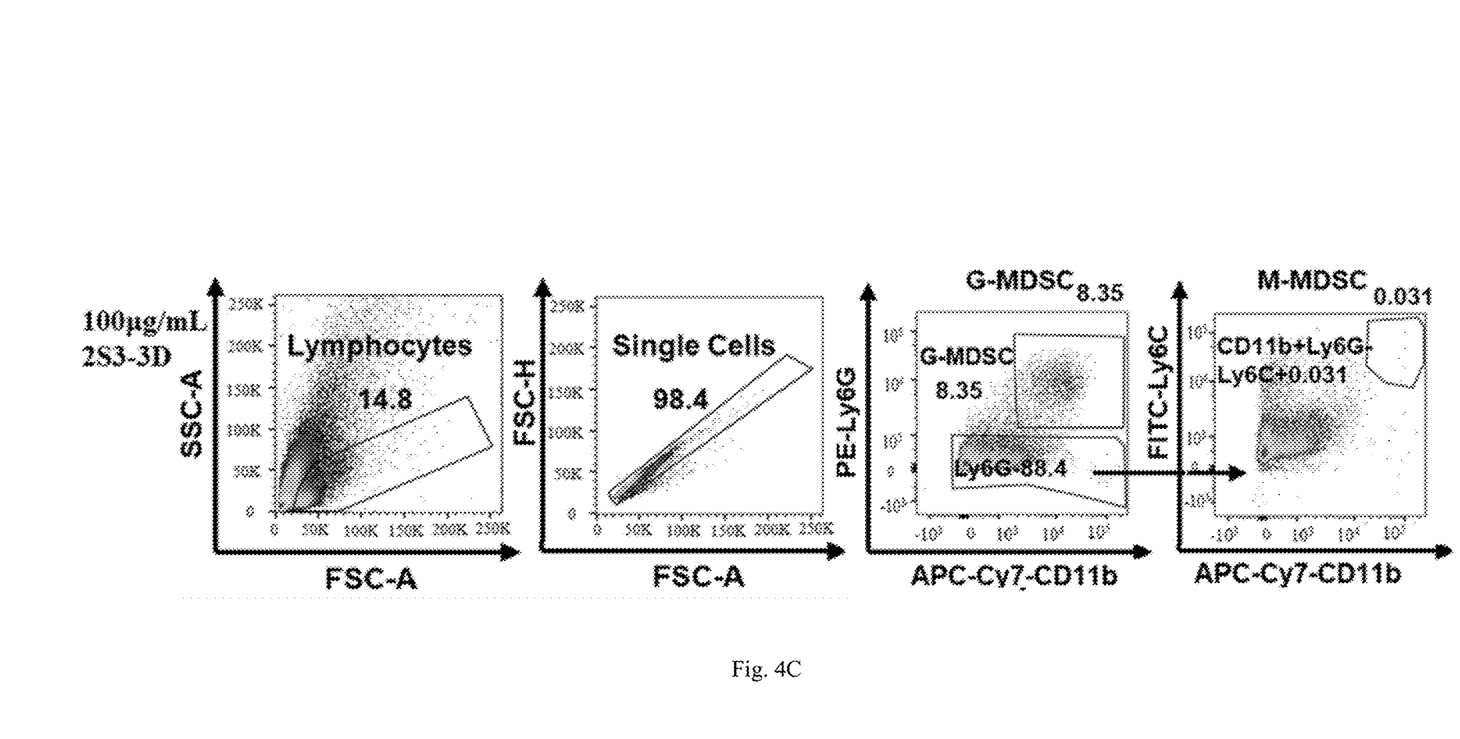
Figure 4D:
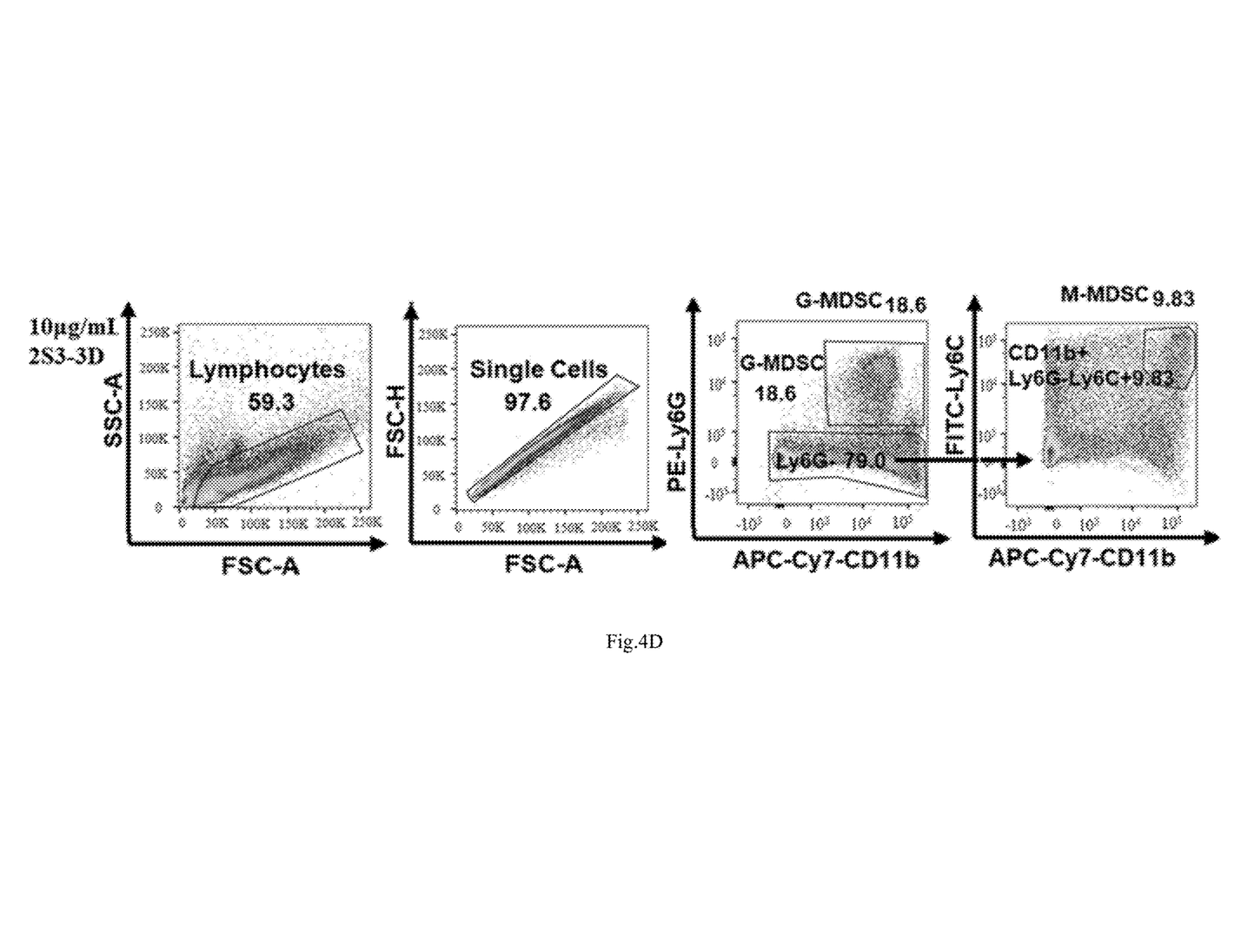
Figure 4E:
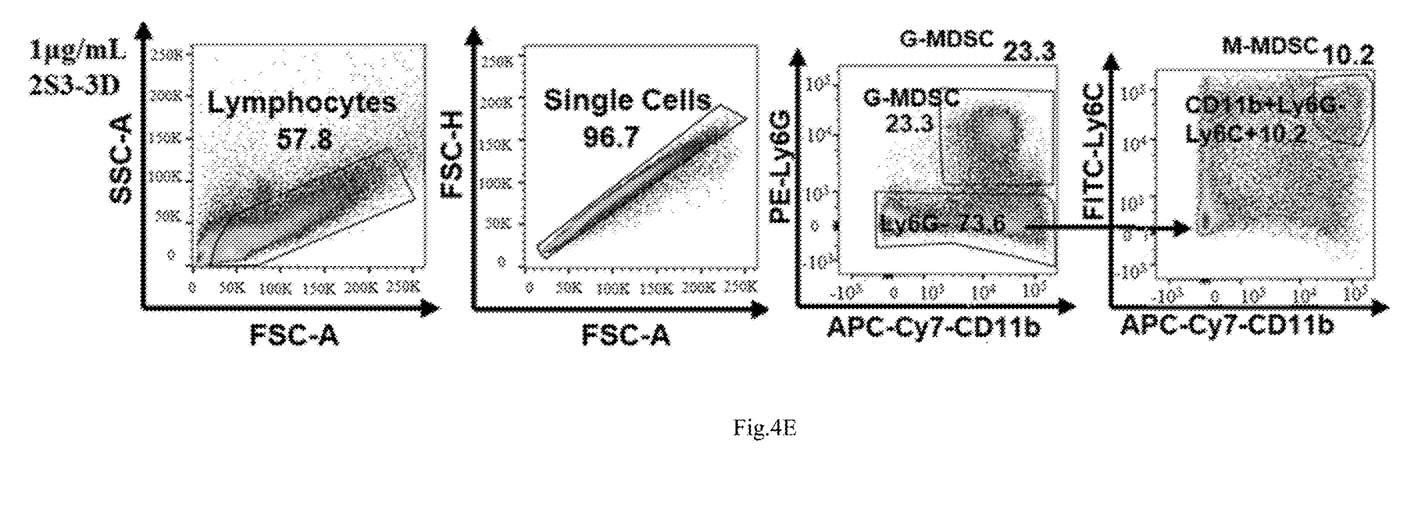
Figure 5:
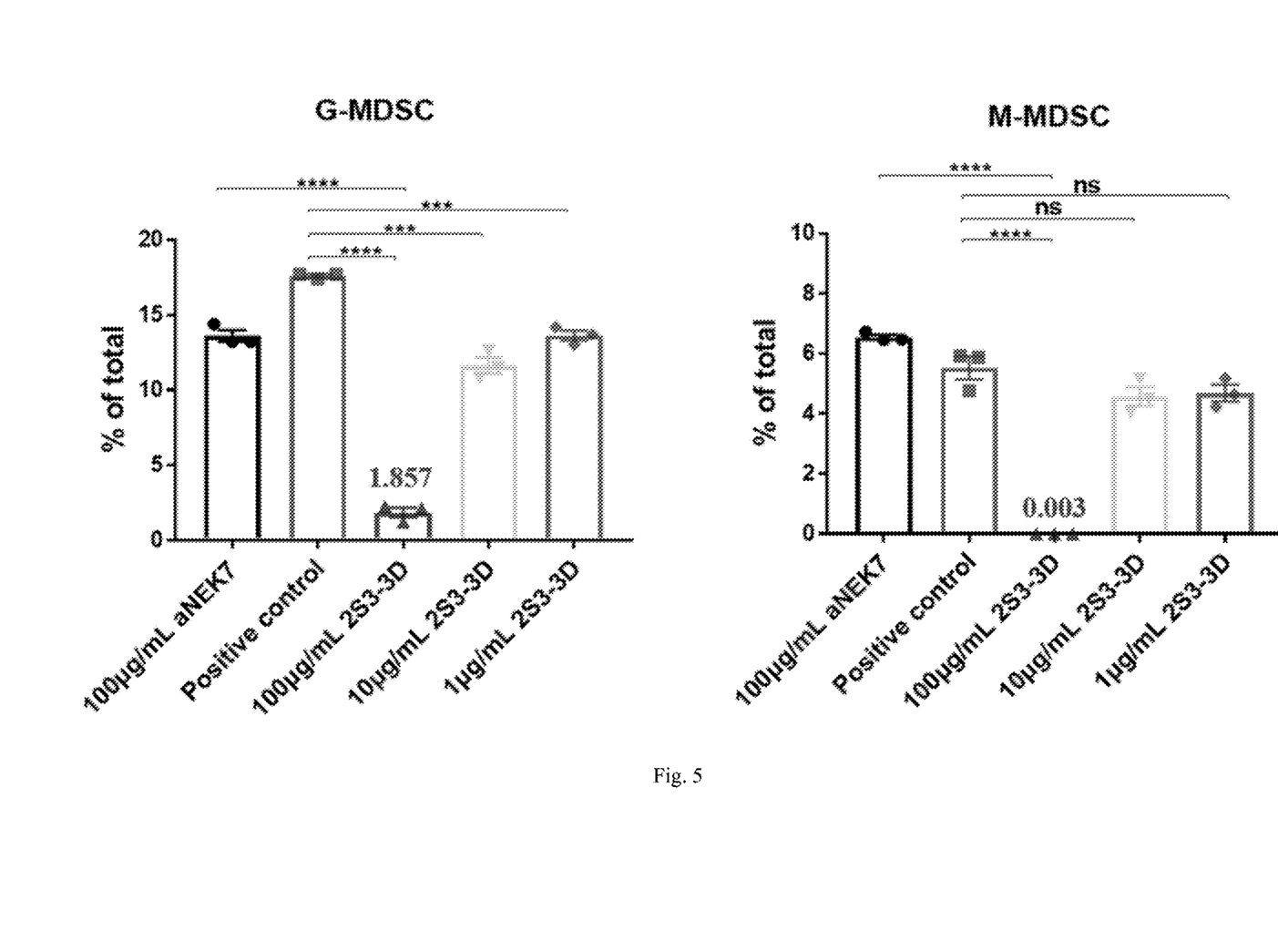
FIG. 5 shows the percentage of MDSC cells after treatment with the nanobody (2S3-3D) detected by means of FACS in Example 8.

The results are shown in FIG. 3, and it can be seen that the nanobody can inhibit the secretion of inflammatory factors.

Example 8 Nanobody Blocking MDSC Differentiation

Two essential cytokines, GM-CSF and IL-6, are required for the developmental differentiation of myeloid precursor cells into MDSC cells in vitro. Since the antibodies herein have cross-species activity, in this Example, the differentiation model of MDSC was constructed in vitro by adding the anti-h-IL-6Rα nanobody to determine whether this nanobody inhibits the IL-6 signaling pathway essential for its differentiation, thereby confirming its biological effect, as follows:

Fresh mouse bone marrow cells were induced to differentiate into MDSC cells using GM-CSF (40 ng/ml, 315-03-20, Peprotech) and IL-6 (40 ng/mL, 575702, Biolegend), and the cells were treated with 100 μg/mL nanobody (2S3-3D) incubated for 4 days in parallel with IL-6 stimulation. The cells were mainly incubated with the corresponding flow antibody for 30 min, and the unbound flow antibody was removed by washing, and finally resuspended with 200 μL of PBS buffer. The proportion of cells was analyzed by flow cytometry of BD to see whether it had an effect on the differentiation of murine-derived MDSC.

The results are shown in FIG. 4A to FIGS. 4E and 5, which show the cell staining, and it was found that the cell proportion of MDSC was significantly reduced after treatment with the nanobody, indicating that the nanobody could prevent the differentiation process of MDSC.

Example 9 Role of Nanobodies in Hepatitis

To further investigate the biological function of the nanobody, a ConA-induced hepatitis model in mice was utilized in this Example for verification. Tail vein injection of Concanavalin A (ConA) induced fulminant hepatitis in mice within 12-24 hours. This autoimmune hepatitis model was mediated by NKT cells and was accompanied by the production of a large number of inflammatory cytokines, including IL-1β, TNF-α, IL-6, IL-12, and the like. It is worth noting that IL-6 did not induce liver injury in this model, but rather played a very protective role. This phenomenon has been confirmed in previous experiments using IL-6 or IL-6R-deficient mice (H Mizuhara et al. J Exp Med 1994; Christian Klein, et al. JCI 2005; Weici Zhang, et al. Hepatology 2010), and IL-6-/-mice showed lower levels of ALT and AST than WT mice. The main mechanism is that IL-6 can stimulate rapid regeneration of liver cells through the gp130-STAT3 signaling pathway, thereby protecting liver cells.

In order to investigate whether the anti-h-IL-6Rα nanobody can inhibit the IL-6 signaling pathway by binding to IL-6Rα, in this Example, C57BL/6 mice were injected intraperitoneally with 500 μg of the nanobody (2S3-3D) per mouse in the above hepatitis model, and then a low dose of Con A was injected into the tail vein 6 hours later, and then the mice were killed 12 hours later and the serum was obtained. The level of ALT in the serum was measured by ELISA.

Figure 6A:
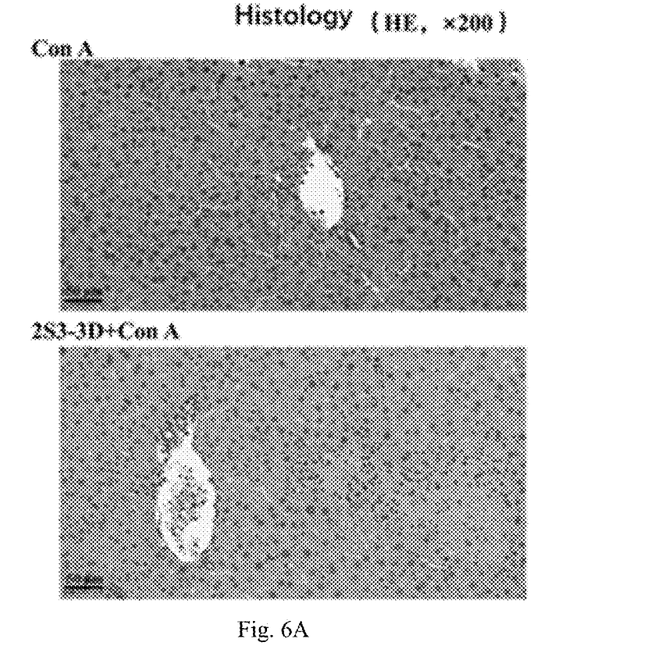
FIGS. 6A and 6B show graphs of the results of evaluating the role of nanobodies in hepatitis by HE staining and ALT assay in Example 9.
Figure 6B:
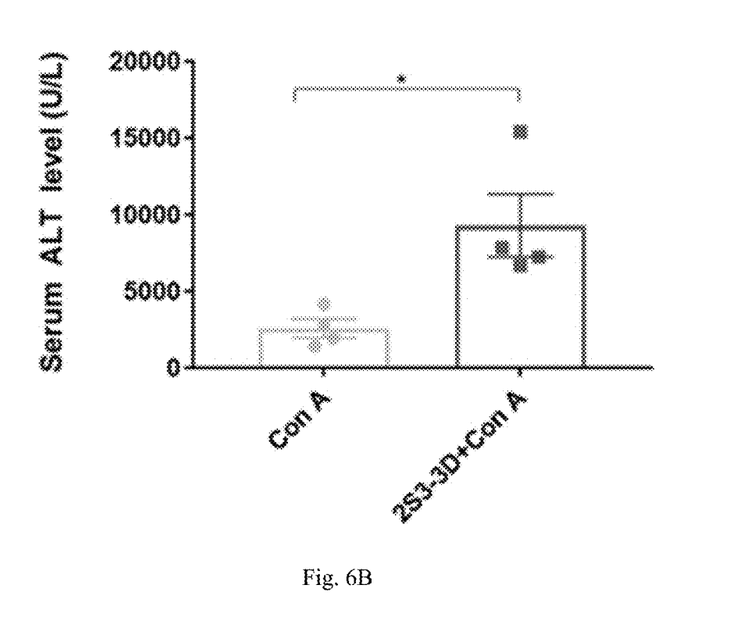

The results are shown in FIGS. 6A and 6B, wherein FIG. 6A shows the results of HE staining of the liver tissues of mice in the Con A group (only tail vein injection of Con A) and the 2S3-3D+Con A group (intraperitoneal injection of 2S3-3D followed by tail vein injection of Con A at 12 h intervals), with a scale bar of 50 μm and a magnification of 200×. FIG. 6B shows the results of ALT levels in serum of the Con A and 2S3-3D+Con A group as measured by the ALT kit. It was found that the WT mice had a higher level of liver damage, and the serum ALT level of the nanobody-treated mice increased significantly, which indicates that the nanobody 2S3-3D of the present invention has the function of inhibiting the IL-6 signaling pathway in this hepatitis model.

The above Examples confirm that the anti-soluble human-derived IL-6Rα nanobody of the present invention has the ability to bind to antigen and has biological functions, such as preventing the secretion of inflammatory factors, preventing MDSC differentiation and other manifestations, and thus can be applied to the development of anti-inflammatory agent and MDSC inhibitor; at the same time, the nanobody has a high affinity for IL-6Rα, and can be applied to the development of IL-6Rα detection reagents or kits, which can provide feasible strategies for the treatment of IL-6 mediated related diseases.

The various technical features of the above-described embodiments can be combined arbitrarily, and in order to make the description concise, all possible combinations of the various technical features of the above-described embodiments have not been described; however, as long as there is no contradiction in the combinations of these technical features, all of them should be regarded as being within the scope of the present specification.

The above-described embodiments express only several embodiments of the present invention, which are described in a more specific and detailed manner, but are not to be construed as a limitation of the patent scope of the invention. It should be pointed out that, for a person of ordinary skill in the art, several deformations and improvements can be made without departing from the conception of the present invention, all of which fall within the scope of protection of the present invention. Therefore, the scope of protection of the patent for the present invention shall be subject to the appended claims.

SEQUENCE LISTING

```
Sequence total quantity: 7
SEQ ID NO: 1            moltype = AA  length = 128
FEATURE                 Location/Qualifiers
source                  1..128
                        mol_type = protein
                        organism = synthetic construct
```

```
SEQUENCE: 1
QLQLVESGGG LVRPGGSLRL SCTIHGVTLD WYAVGWFRQA PGKEREGVSC ISSSDGSTYY    60
ADSVKGRFTI SRDNVKNTMY LQMNSLKPED TAVYYCAMVF TTAQAMGVPF HDFEYDYWGP   120
GTQVTVSS                                                            128

SEQ ID NO: 2            moltype = AA  length = 12
FEATURE                 Location/Qualifiers
source                  1..12
                        mol_type = protein
                        organism = synthetic construct
SEQUENCE: 2
TIHGVTLDWY AV                                                        12

SEQ ID NO: 3            moltype = AA  length = 7
FEATURE                 Location/Qualifiers
source                  1..7
                        mol_type = protein
                        organism = synthetic construct
SEQUENCE: 3
ISSSDGS                                                               7

SEQ ID NO: 4            moltype = AA  length = 22
FEATURE                 Location/Qualifiers
source                  1..22
                        mol_type = protein
                        organism = synthetic construct
SEQUENCE: 4
AMVFTTAQAM GVPFHDFEYD YW                                             22

SEQ ID NO: 5            moltype = AA  length = 231
FEATURE                 Location/Qualifiers
source                  1..231
                        mol_type = protein
                        organism = synthetic construct
SEQUENCE: 5
PKSCDKTHTC PPCPAPELLG GPSVFLFPPK PKDTLMISRT PEVTCVVVDV SHEDPEVKFN    60
WYVDGVEVHN AKTKPREEQY NSTYRVVSVL TVLHQDWLNG KEYKCKVSNK ALPAPIEKTI   120
SKAKGQPREP QVYTLPPSRD ELTKNQVSLT CLVKGFYPSD IAVEWESNGQ PENNYKTTPP   180
VLDSDGSFFL YSKLTVDKSR WQQGNVFSCS VMHEALHNHY TQKSLSLSPG K            231

SEQ ID NO: 6            moltype = AA  length = 359
FEATURE                 Location/Qualifiers
source                  1..359
                        mol_type = protein
                        organism = synthetic construct
SEQUENCE: 6
QLQLVESGGG LVRPGGSLRL SCTIHGVTLD WYAVGWFRQA PGKEREGVSC ISSSDGSTYY    60
ADSVKGRFTI SRDNVKNTMY LQMNSLKPED TAVYYCAMVF TTAQAMGVPF HDFEYDYWGP   120
GTQVTVSSPK SCDKTHTCPP CPAPELLGGP SVFLFPPKPK DTLMISRTPE VTCVVVDVSH   180
EDPEVKFNWY VDGVEVHNAK TKPREEQYNS TYRVVSVLTV LHQDWLNGKE YKCKVSNKAL   240
PAPIEKTISK AKGQPREPQV YTLPPSRDEL TKNQVSLTCL VKGFYPSDIA VEWESNGQPE   300
NNYKTTPPVL DSDGSFFLYS KLTVDKSRWQ QGNVFSCSVM HEALHNHYTQ KSLSLSPGK    359

SEQ ID NO: 7            moltype = AA  length = 5
FEATURE                 Location/Qualifiers
source                  1..5
                        mol_type = protein
                        organism = synthetic construct
SEQUENCE: 7
GGGGS                                                                 5
```

What is claimed is:

1. A nanobody targeting an IL-6Rα protein, wherein the nanobody comprises a heavy chain variable region comprising CDR1 of SEQ ID NO.2, CDR2 of SEQ ID NO.3, and CDR3 of SEQ ID NO.4.

2. The nanobody targeting an IL-6Rα protein of claim 1, wherein the nanobody has the amino acid sequence of SEQ ID NO. 1.

3. The nanobody targeting an IL-6Rα protein of claim 1, wherein the nanobody further comprises an Fc domain of IgG.

4. The nanobody targeting an IL-6Rα protein of claim 3, wherein the Fc domain is an IgG1 Fc domain.

5. The nanobody targeting an IL-6Rα protein of claim 4, wherein the IgG1 Fc domain is a human IgG1 Fc domain.

6. The nanobody targeting an IL-6Rα protein of claim 5, wherein the amino acid sequence of the human IgG1 Fc domain is as shown in SEQ ID NO.5.

7. The nanobody targeting an IL-6Rα protein of claim 6, wherein the amino acid sequence of the nanobody is shown in SEQ ID NO.6.

8. A nucleotide molecule encoding the nanobody of claim 1.

9. An expression vector, wherein the expression vector contains the nucleotide molecule of claim 8.

10. A host cell, wherein the host cell is a host cell for expression of an exogenous protein, which contains the expression vector of claim 9.

11. The host cell of claim 10, wherein the host cell is a bacterial, yeast, insect cell, or mammalian cell.

12. A pharmaceutical composition, wherein the pharmaceutical composition comprises the nanobody of claim 1, further comprising at least one pharmaceutically acceptable excipient.

13. The nanobody targeting an IL-6Rα protein of claim 1, wherein the IL-6Rα protein is a human-derived IL-6Rα protein or a murine-derived IL-6Rα protein.

* * * * *